US008617228B2

(12) United States Patent
Wittenberger et al.

(10) Patent No.: US 8,617,228 B2
(45) Date of Patent: Dec. 31, 2013

(54) METHOD AND SYSTEM FOR PREVENTING NERVE INJURY DURING A MEDICAL PROCEDURE

(75) Inventors: Dan Wittenberger, L'ile Bizard (CA); Nicolas Coulombe, Montreal (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 621 days.

(21) Appl. No.: 12/604,882

(22) Filed: Oct. 23, 2009

(65) Prior Publication Data
US 2011/0098761 A1 Apr. 28, 2011

(51) Int. Cl.
*A61N 1/02* (2006.01)
(52) U.S. Cl.
USPC .......................................................... 607/96
(58) Field of Classification Search
USPC .................................................. 607/69–99, 2
See application file for complete search history.

(56) References Cited

U.S. PATENT DOCUMENTS

| 4,776,338 | A | * | 10/1988 | Lekholm et al. ............... 607/24 |
| 5,782,826 | A | | 7/1998 | Swanson |
| 7,299,093 | B2 | | 11/2007 | Zhu et al. |
| 2004/0122482 | A1 | * | 6/2004 | Tung et al. .................... 607/48 |
| 2005/0215990 | A1 | | 9/2005 | Govari |
| 2009/0043352 | A1 | | 2/2009 | Brooke et al. |
| 2009/0088827 | A1 | | 4/2009 | Tockman et al. |
| 2009/0182318 | A1 | | 7/2009 | Abboud et al. |

FOREIGN PATENT DOCUMENTS

| EP | 0573311 A1 | 6/1993 |
| WO | 0038574 A1 | 7/2000 |
| WO | 2004056267 A1 | 7/2004 |
| WO | 2008116232 A1 | 9/2008 |

OTHER PUBLICATIONS

Antz Matthius et al. "Ablation of Atrial Fibrillation in Humans Using a Balloon-Based Ablation System: Identification of the site of the phrenic nerve damage using pacing maneuvers and Carto," Journal of Cardiovascular Electrophysiology, vol. 17, No. 11, Nov. 2006, pp. 1242-1245, XP00262917, Issn: 1045-3873.
Baghat Hemant et al. "Capnography as an Aid in Localizing the Phrenic Nerve in Brachial Plexus Surgery. Technical note," Journal of Brachial Plexus and Peripheral Nerve Injury, Biomed Central Ltd, LO, vol. 3, No. 1, May 22, 2008, p. 14, XP021039627, Issn: 1749-7221.

* cited by examiner

*Primary Examiner* — Amanda Patton
(74) *Attorney, Agent, or Firm* — Christopher & Weisberg, P.A.

(57) ABSTRACT

A method of treating tissue is provided, including positioning a stimulation device proximate a phrenic nerve; stimulating the phrenic nerve with the stimulation device; measuring a physiological response to the stimulation; defining a threshold physiological response value based at least in part on the measured physiological response; positioning a thermal treatment element proximate to an arrhythmogenic cardiac tissue region; applying a thermal treatment regimen to the cardiac tissue region with the medical device; measuring a physiological parameter during the thermal treatment regimen application; and conveying the measured physiological parameter to a controller, the controller comparing the measured physiological parameter to the defined physiological response value threshold, the controller adjusting the thermal treatment regimen in response to the comparison of the measured physiological parameter to the defined physiological response value threshold.

7 Claims, 7 Drawing Sheets

METHOD AND SYSTEM FOR PREVENTING NERVE INJURY DURING A MEDICAL PROCEDURE

CROSS-REFERENCE TO RELATED APPLICATION

N/A

STATEMENT REGARDING FEDERAL SPONSORED RESEARCH OR DEVELOPMENT

N/A

FIELD OF THE INVENTION

The present invention relates to a method and system for preventing nerve injury during a medical procedure.

BACKGROUND OF THE INVENTION

When treating particular regions of tissue, through thermal energy interaction or the like for example, it may be difficult to direct or control the depth and intensity of the heat transfer. The delivery of thermal energy or other therapeutic modality may not be necessarily contained to the exact region or depth desired for treatment, as the tissue may have varying therapy-conducive properties affected by the surrounding physiological environment. While thermal control or precision may be of more concern with certain treatment modalities, such as radiofrequency or microwave treatment procedures, it is often desirable to limit thermal treatment or exposure to just the tissue desired. Failure to do so may otherwise negatively and adversely affect surrounding tissue structures or organs that are sensitive and susceptible to undesired damage.

For example, when attempting to treat cardiac tissue, sensitive tissue structures abound that may react adversely to thermal applications. In particular, when thermally treating or ablating tissue in or about the heart, it is essential that critical physiological structures such as the phrenic nerve, sinoatrial node, and the like are not inadvertently destroyed through such ablation therapy. The phrenic nerve is made up mostly of motor nerve fibers that produce contractions of the diaphragm and thus affect breathing and respiration patterns and conditions. In addition, the phrenic nerve provides sensory innervation for many components of the mediastinum and pleura, as well as the upper abdomen, especially the liver, and the gall bladder.

The phrenic nerve is generally referred to in two segments: the right and left phrenic nerves. Both phrenic nerves run from C3, C4 and C5 vertebrae along the anterior scalene muscle deep to the carotid sheath. The right phrenic nerve passes over the brachlocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium. The left phrenic nerve passes over the pericardium of the left ventricle and pierces the diaphragm separately.

Referring to FIGS. 1-3, the close proximity of the phrenic nerve segments to the right atrium and left ventricle is illustrated. These cardiac regions may be the location or origin of heart arrhythmias or other physiological maladies and thus targeted for tissue ablation in order to remove or otherwise remedy the abnormal electrophysiological occurrence. In thermally treating or ablating select cardiac regions, the phrenic nerve may be at risk of being similarly, although unintentionally, ablated. This could severely impact the normal respiratory functioning of the patient. The risk of such unintentional and undesirable destruction or application of thermal energy to this and other cursory structures compels a desire to monitor or otherwise detect potentially-damaging consequences during treatment.

SUMMARY OF THE INVENTION

The present invention advantageously provides a method and system to monitor or otherwise detect potentially-damaging consequences during treatment of sensitive tissue areas. In particular, a method of treating cardiac tissue is provided, including stimulating a target tissue structure; measuring a physiological response to the stimulation; defining a threshold physiological response value based at least in part on the measured physiological response; applying a thermal treatment regimen to a tissue region; measuring a physiological parameter during the thermal treatment regimen application; comparing the measured physiological parameter to the defined physiological response value threshold; and adjusting the thermal treatment regimen in response to the comparison of the measured physiological parameter to the defined physiological response value threshold. The target tissue structure may include a phrenic nerve, and measuring the physiological response may include at least one of an electromyography measurement, a mechanomyography measurement, a kinemyography measurement, an end-tidal carbon dioxide measurement, a transthoracic impedance measurement and a pulse oximetry measurement. The method may include generating an alert in response to the comparison between the measured physiological parameter to the defined physiological response value threshold; and thermally treating a tissue region can include cryoablation of the tissue region or heat-based ablation (e.g., radiofrequency, laser, microwave, etc.) of the tissue region. Stimulating the target tissue can include the application of at least one of electrical energy and magnetic energy. Also, adjusting the thermal treatment regimen can include increasing the temperature of the tissue region (such as in the case of radiofrequency, microwave, ultrasound or laser ablation), decreasing the temperature of the tissue region (during cryoablation), or discontinuing treatment.

A method of treating tissue is also provided, including positioning a stimulation device proximate a phrenic nerve; stimulating the phrenic nerve with the stimulation device; measuring a physiological response to the stimulation; defining a threshold physiological response value based at least in part on the measured physiological response; positioning a thermal treatment element proximate to a target cardiac tissue region (such as an arrhythmogenic site); applying a thermal treatment regimen to the cardiac tissue region with the medical device; measuring a physiological parameter during the thermal treatment regimen application; and conveying the measured physiological parameter to a controller, the controller comparing the measured physiological parameter to the defined physiological response value threshold, the controller adjusting (or providing the physician with indications to adjust or terminate) the thermal treatment regimen in response to the comparison of the measured physiological parameter to the defined physiological response value threshold.

A medical system is also provided, including a stimulation device operable to apply an excitation energy to a target tissue structure; an assessment device operable to measure a physiological condition resulting from an applied excitation energy; a medical device having a thermal treatment element; and a controller in communication with the assessment device and the medical device, the controller adjusting the operation of the thermal treatment element based at least in part on a measured physiological condition measured by the assessment device. The assessment device can include an electromyograph, a mechanomyograph, a kinemyograph, an end-tidal carbon dioxide sensor, an impedance pneumograph and a pulse oximeter. A console may be included, the console including the controller, a thermal energy source and/or an excitation energy source in communication with the stimulation device. The thermally conductive region of the medical device can include a balloon and a cryogenic coolant flow path therethrough, and/or an electrode.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
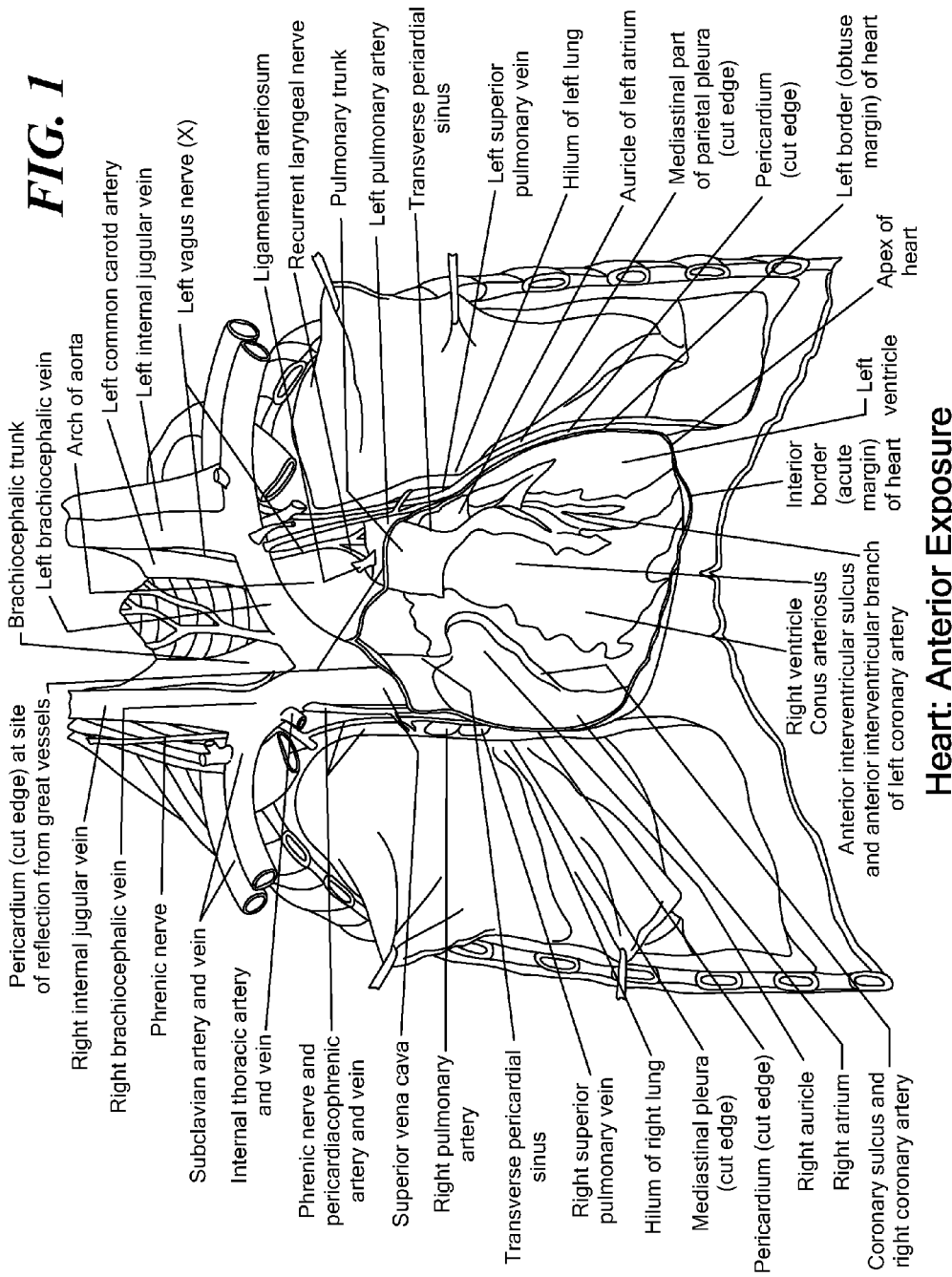
FIG. 1 is an anterior illustration of a thoracic region and related anatomy.
Figure 2:
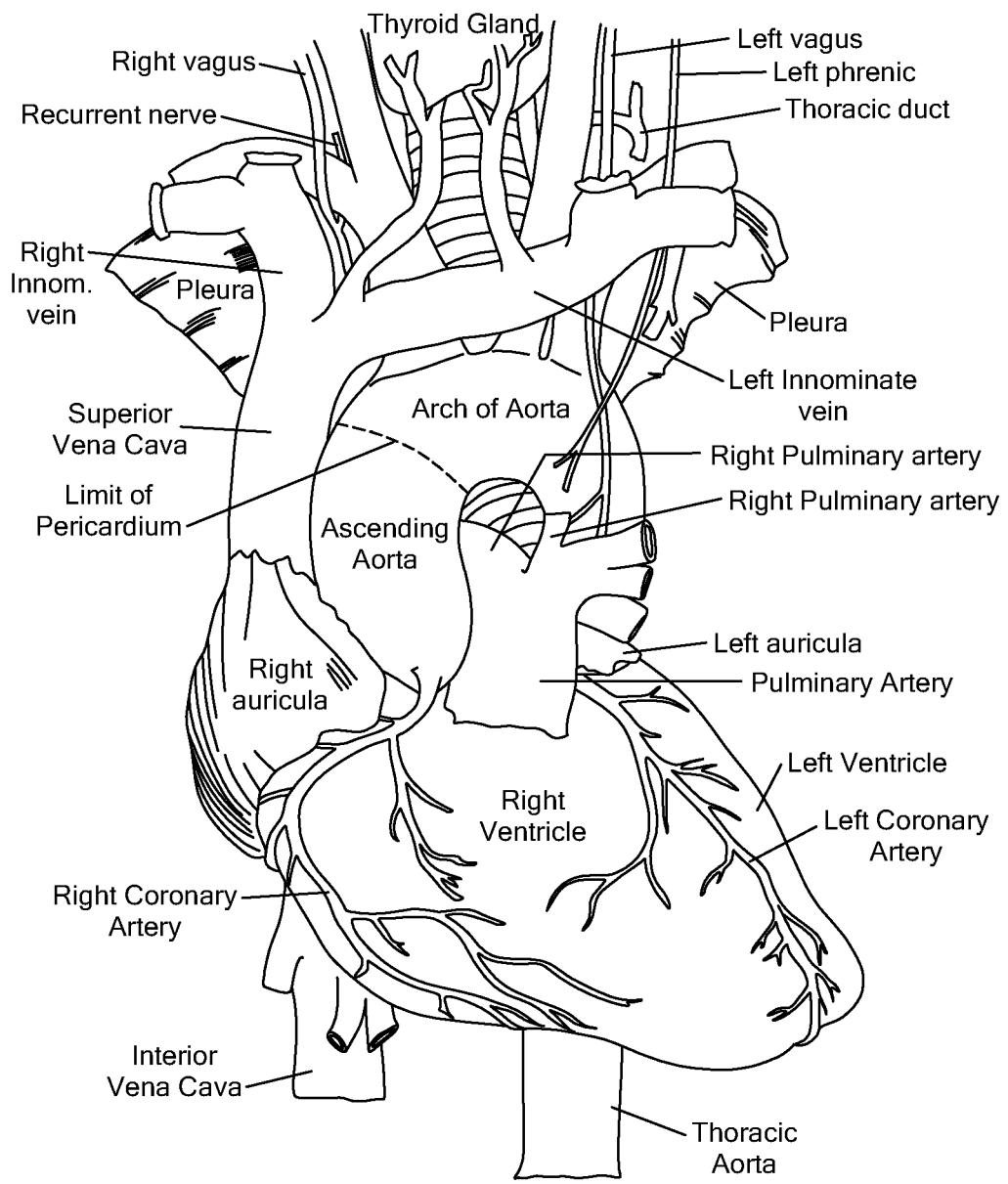
FIG. 2 is an illustration of a human heart and related anatomy.
Figure 3:
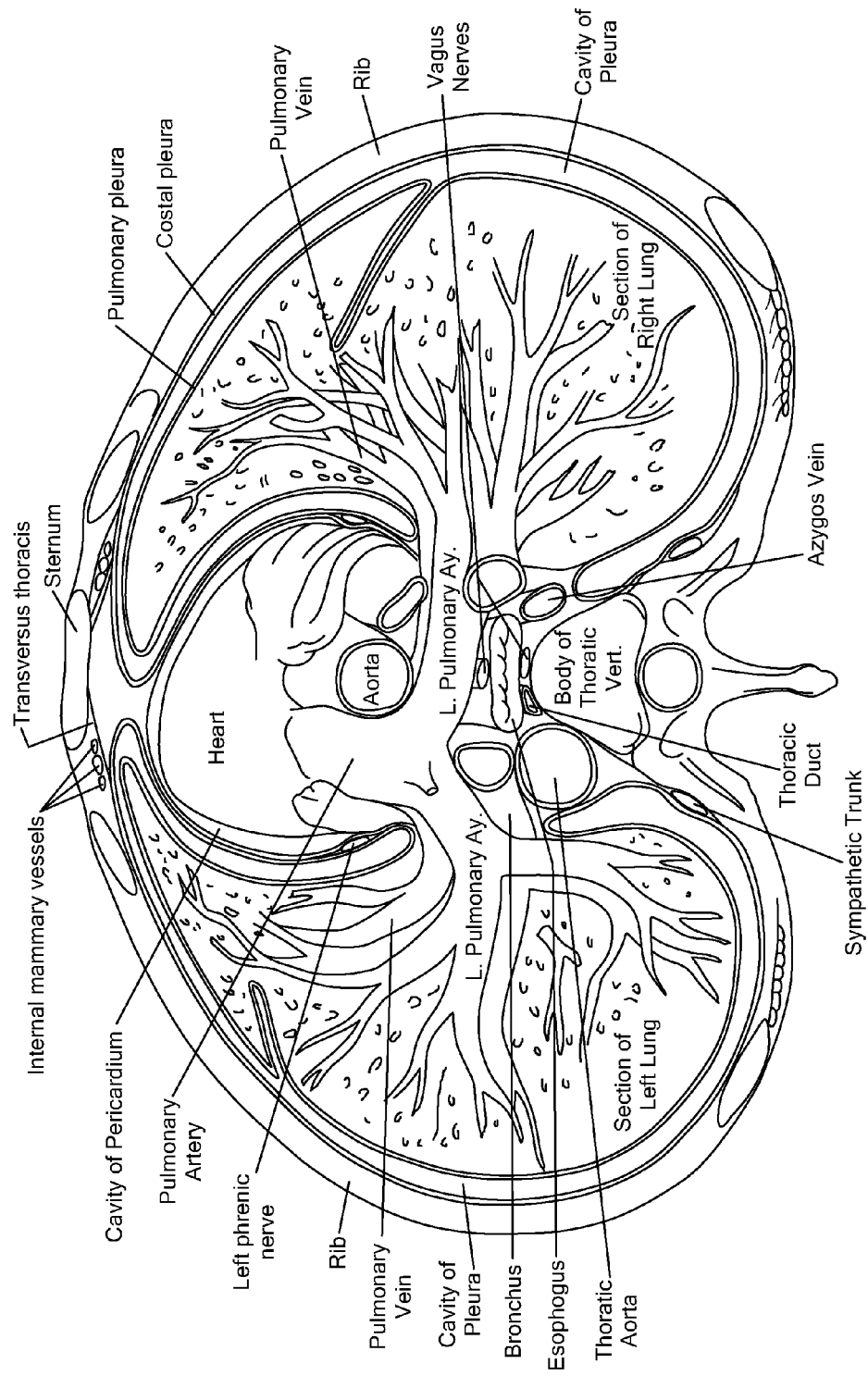
FIG. 3 is an additional illustration of a human heart and related anatomy.
Figure 4:
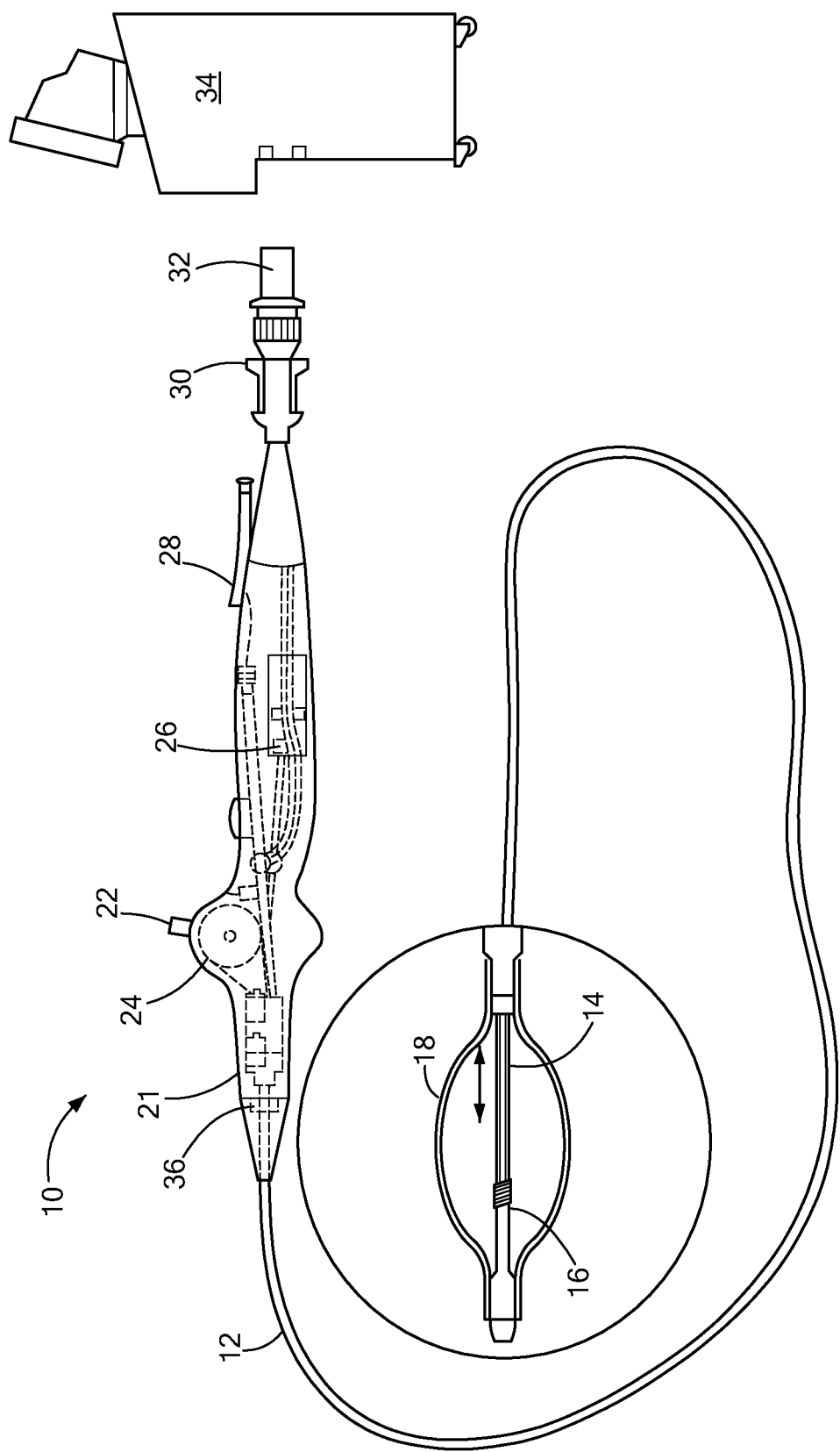
FIG. 4 is an illustration of a medical device system constructed in accordance with the principles of the present invention.
Figure 5:
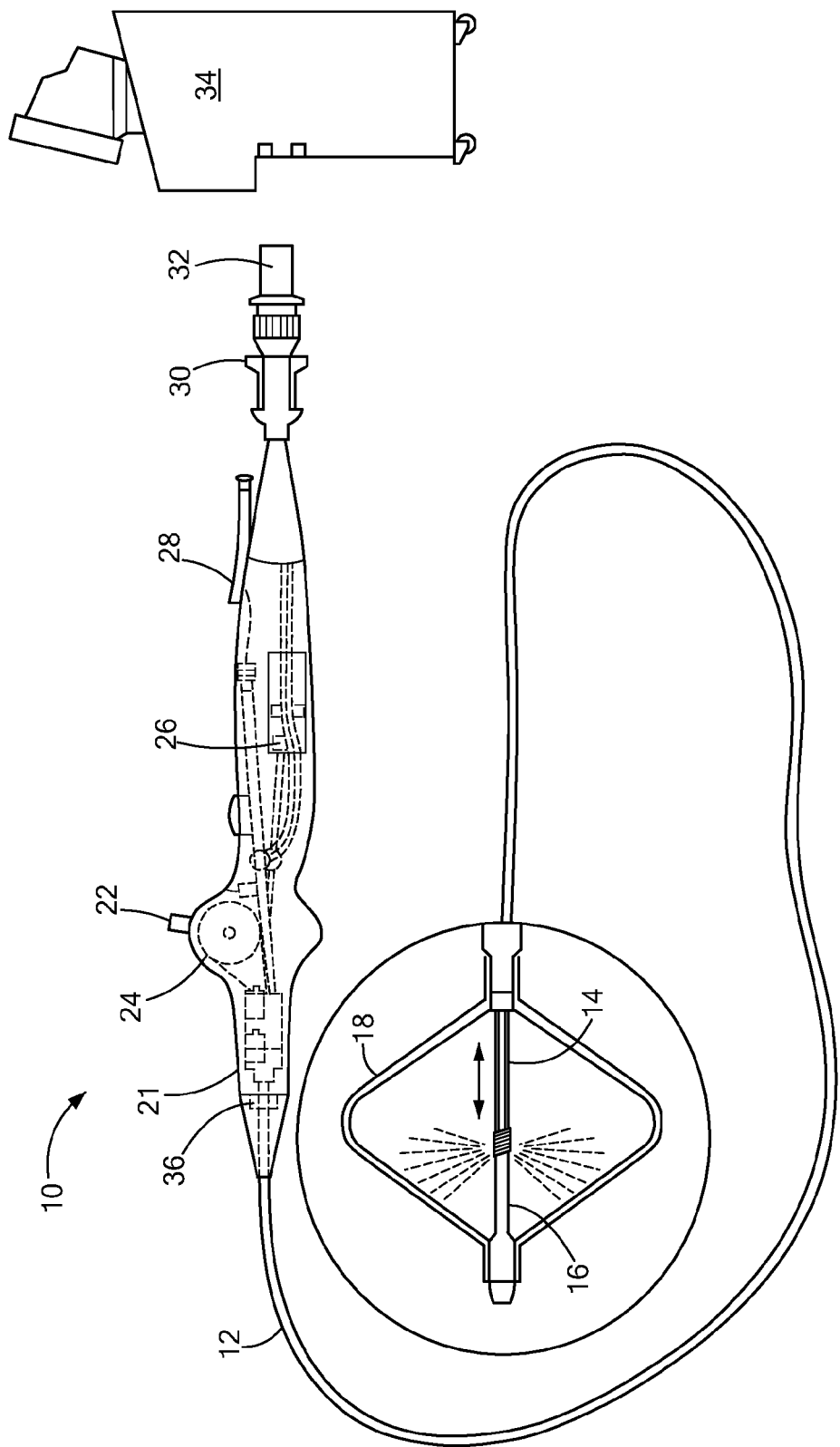
FIG. 5 is another illustration of a medical device system constructed in accordance with the principles of the present invention.

The present invention advantageously provides a method and system to monitor or otherwise detect potentially-damaging consequences during treatment of sensitive tissue areas. In particular, as shown in the accompanying figures in which like reference designators refer to like components, a medical device of a medical treatment system is shown in FIGS. 4-5, generally designated as '10'. The medical device 10 may include an elongate body 12, such as a catheter. The elongate body 12 may define a proximal portion and a distal portion, and may further include one or more lumens disposed within the elongate body 12 to provide mechanical, electrical, and/or fluid communication between the proximal portion of the elongate body 12 and the distal portion of the elongate body 12. For example, the elongate body 12 may include an injection lumen 14 and an exhaust lumen defining a fluid flow path therethrough. In addition, the elongate body 12 may include a guidewire lumen 16 movably disposed within and/or extending along at least a portion of the length of the elongate body 12 for over-the-wire applications. The guidewire lumen 16 may define a proximal end and a distal end, and the guidewire lumen 16 may be movably disposed within the elongate body 12 such that the distal end of the guidewire lumen 16 extends beyond and out of the distal portion of the elongate body 12.

The medical device 10 of the present invention may further include a treatment element 18 at least partially disposed on the elongate catheter body to provide thermal treatment (such as radiofrequency energy or cryogenic treatment) to a selected tissue area. The treatment element 18 may include one or more balloons or other expandable structure defining a proximal end coupled to the distal portion of the elongate body 12 of the catheter, while further defining a distal end coupled to the distal end of the guidewire lumen 16. As such, due to the movable nature of the guidewire lumen 16 about the elongate body 12, any axial and/or longitudinal movement of the guidewire lumen 16 may act to tension or loosen the treatment element 18, i.e., extend or retract the treatment element 18 from a lengthened state to a shortened state during deflation or inflation, respectively. In addition, the treatment element 18 may have any of a myriad of shapes, and may further include one or more material layers providing for safety, puncture resistance, radiopacity, or the like. The treatment element 18 may be coupled to an energy and/or treatment source, such as a radiofrequency generator or source of cryogenic coolant. The treatment element 18 may be in communication with the fluid injection and exhaust lumens of the medical device 10 as described above. The lumens can define a fluid flow path to provide a treatment fluid, such as a cryogenic fluid or the like, to the interior of the treatment element 18. In addition, a sheath (not shown) may be provided which is slidably positionable about at least a portion of the elongate body 12 of the medical device 10 and/or the treatment element 18. One or more electrodes or other thermally and/or electrically conductive portions (not shown) may also be disposed about or otherwise coupled to the treatment element 18.

The medical device 10 may include a handle element 21 coupled to the proximal portion of the elongate body 12, where the handle may include an element such as a lever or knob 22 for manipulating the catheter body and/or additional components of the medical device 10. For example, a pull wire with a proximal end and a distal end may have its distal end anchored to the elongate body 12 at or near the distal end. The proximal end of the pull wire may be anchored to an element such as a cam 24 in communication with and responsive to the lever. The handle 21 can further include circuitry for identification and/or use in controlling of the medical device 10 or another component of the system. For example, the handle may include one or more pressure sensors 26 to monitor the fluid pressure within the medical device 10. Additionally, the handle may be provided with a fitting 28 for receiving a guidewire that may be passed into the guidewire lumen 16, which may be partially disposed within the elongate body 12.

The handle 21 may also include connectors that are matable directly to a fluid supply/exhaust and/or control unit by way of one or more umbilicals for providing fluid communication with the second elongate body 12. For example, the handle may be provided with a first connector 30 that is matable with a co-axial fluid umbilical (not shown) and a second connector 32 that is matable with an electrical umbilical (not shown) that can further include an accessory box (not shown). In an exemplary system, a fluid supply and exhaust, as well as various control mechanisms for the system may be housed in a single console or control unit 34. In addition to providing an exhaust function for the catheter fluid supply, the console 34 may also recover and/or re-circulate fluid delivered to the handle 20 and the elongate body 12 of the medical device 10. A vacuum pump in the console may create a low-pressure environment in one or more conduits within the catheter body so that fluid is drawn into the conduit(s), away from the treatment element 18, and towards the proximal end of the catheter. The console 34 may also house one or more alternative energy sources to supply the selected modality of treatment to the treatment element 18, such as, for example, a radiofrequency generator, ultrasound generator, light sources, or the like.

The system of the present invention may further include the stimulation, measuring and/or monitoring of a physiological condition of a patient, as well as subsequent triggering or actuation of one or more predetermined, automated protocols or procedures in response to the monitored/measured condition. For example, the system may provide for the stimulation of the phrenic nerve via one or more clinical modalities to measure an induced response. As discussed above, the phrenic nerve is a sensitive physiological structure located in the vicinity of cardiac tissue that may be targeted for one or more treatment applications (such as ablation to treat an arrhythmia, for example). The induced response may then be used to establish or otherwise define a threshold or baseline value. Subsequent activity or physiological changes occurring in the patient during a therapeutic procedure may be compared to the baseline or threshold value and thus used to modify one or more parameters of the delivered treatment.

Figure 6:
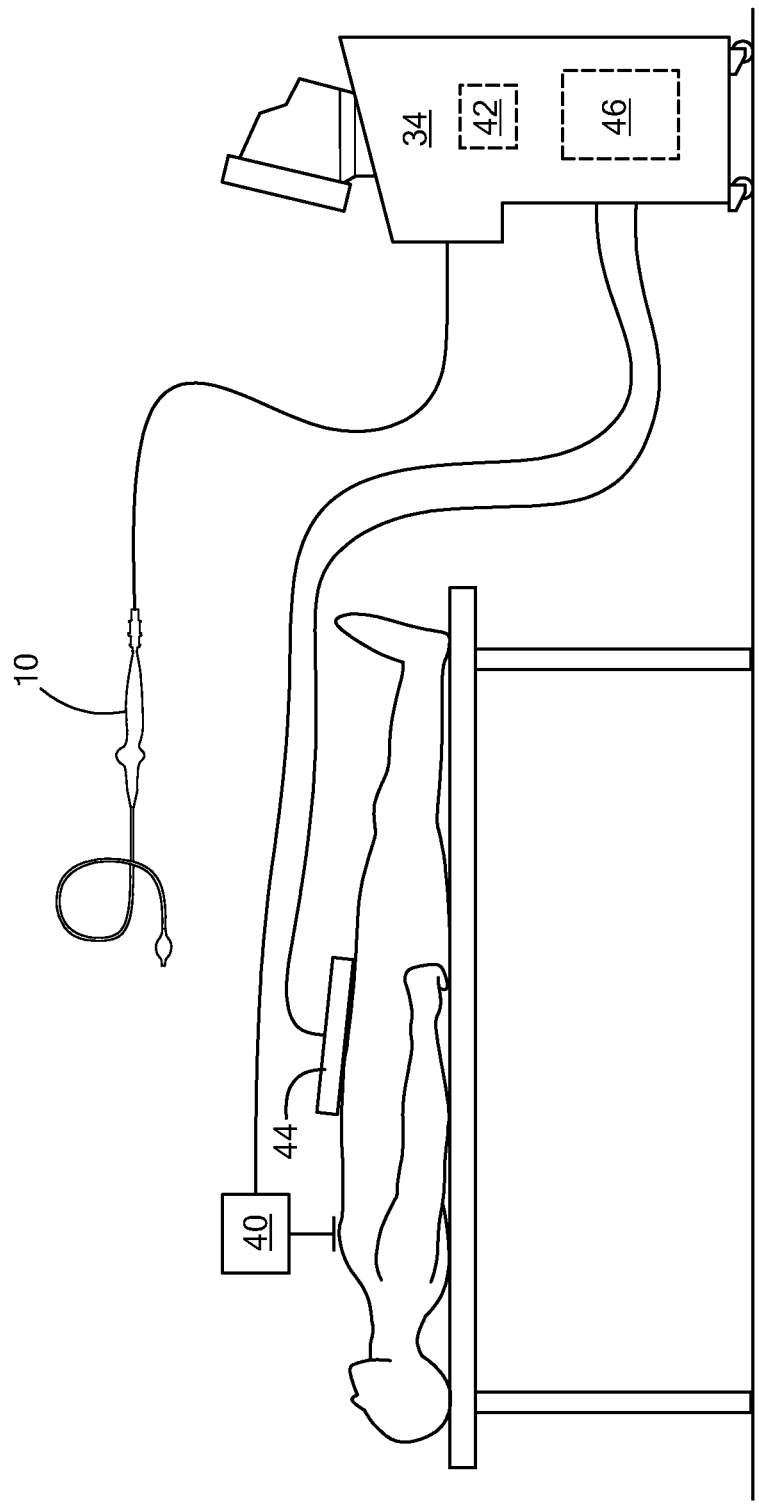
FIG. 6 is yet another illustration of a medical device system constructed in accordance with the principles of the present invention.

Now referring to FIG. 6, the medical system of the present invention may include a stimulation device 40 for exciting or stimulating a stimulation target tissue area or structure, such as the phrenic nerve, proximal to the ablation site. The stimulation device 40 may provide the controlled delivery of electrical and/or magnetic impulses to the targeted tissue. The stimulation device 40 may include one or more electrically and/or magnetically conductive portions in proximity to the targeted tissue structure for stimulation delivery. For example, one or more electrodes or leads may be positioned on the patient and/or a minimally-invasive or surgical device having conductive elements thereon may be positioned about the stimulation targeted structure to deliver the stimulating pulse or energy. The electrodes or electrically/magnetically conducive elements may be coupled to an energy source 42 providing the stimulating energy. A controller and/or processing components may also be included to control, adjust, or otherwise manipulate and select the appropriate energy to be delivered to accomplish the subsequent stimulation or excitation of the targeted tissue structure. The excitation energy source, controller, and/or processor may be housed within or otherwise provided as part of the console, with the stimulation device being releasably coupled to the console during operation thereof.

An assessment device 44 may also be included in the present system for measuring, monitoring, or otherwise assessing a physiological activity or response resulting from an applied stimulation and relaying the accumulated information for further action. For example, upon excitation of the phrenic nerve, the response may include a contraction of the diaphragm of the patient. The assessment device 44 operates to measure, monitor, or otherwise assess one or more quantifiable parameters resulting from the excitation and contraction, such as the amplitude of the diaphragm motion, electrical signals measured at other locations in the patient, and/or respiratory parameters, for example. Such respiratory patterns or conditions may then be used to infer or monitor the condition or status of the phrenic nerve (which affects/controls breathing, as discussed above), and whether or not the phrenic nerve is being adversely or unintentionally affected during a particular treatment procedure.

In particular, the assessment device 44 may monitor or record electromyography ("EMG") measurements. An electromyograph detects the electrical potential generated by muscle cells when these cells are both mechanically active and at rest. To perform intramuscular EMG, an electrode may be inserted through the skin into the muscle tissue. Subsequently, electrical signals may be taken upon contraction of the muscle (such as in response to the induced excitation of the targeted tissue structure) and again during relaxation. The shape, size and frequency of the resulting muscle motor unit potentials can then be analyzed to establish a baseline or threshold value for later comparison. In cases where intramuscular EMG may be considered too invasive or unnecessary, a surface electrode may be used to monitor the muscle activation. The assessment device 44 may also include quantifying, monitoring or recording of contraction or muscle activity through mechanomyography methods and/or kinemyography methods using sensors and transducers placed on or about the patient.

The assessment device 44 may also quantify, monitor and/or record respiratory parameters, such as exhalation characteristics. For example, carbon dioxide is produced by cellular metabolism and is transported to the right heart by the venous system. It is then pumped into the lungs by the heart and then diffuses out into the exhaled air, where it can be measured. End-tidal carbon dioxide ("EtCO2") measurements reflect metabolism, circulation and ventilation. The assessment device 44 may thus include one or more sensors for taking EtCO2 measurements resulting after the delivered excitation to a targeted tissue structure.

The assessment device 44 may further provide bioelectrical impedance measurements. For example, impedance pneumography allows for the continuous, noninvasive measurement of breathing. The principle of this technique involves the measurement of respiration from electrical impedance changes in the chest. In biological tissues, electrical current is carried by ions, the concentration of which is relatively constant. An impedance measurement may be taken that modulates a carrier waveform passed through the chest between a plurality of electrodes to produce an output that varies with respiration. Measurement of the impedance values across the thoracic cavity or region thus can be used to discern or otherwise calculate respiratory conditions or patterns, such as breathing rate or volume.

The assessment device 44 may further provide pulse oximetry measurements or indications. Pulse oximetry allows noninvasive monitoring of the oxygenation of a patient's hemoglobin. The assessment device 44 may include a sensor positionable on a thin part of the patient's anatomy, such as a fingertip or earlobe, and subsequently pass light containing both red and infrared wavelengths from one side of the anatomy to the other. The changing absorbance of each of the two wavelengths may then be measured, allowing a determination of the absorbances due to the pulsing arteria blood. Based upon the ratio of changing absorbance of the red and infrared light caused by the difference in color between oxygen-bound (bright red) and oxygen unbound (dark red or blue, in severe cases) blood hemoglobin, a measure of oxygenation (the percent of hemoglobin molecules bound with oxygen molecules) can be made, and correlated to a breathing condition or status of the phrenic nerve.

The assessment device 44 may provide the assessed, monitored, or otherwise measured information to a controller, processor or other computational/analytical component 46. The obtained information may then be used to determine any appropriate action responsive to the measured characteristics. For example, the delivery of therapeutic energy or treatment may be automatically altered in response to the information provided by the assessment device, as discussed in more detail below, or the system could provide the physician with indications to adjust or terminate the thermal treatment regimen. The controller, processor, and/or related hardware and software components affecting a predetermined course of action based on the information provided by the assessment device may be contained within or otherwise provided with the console 34.

Figure 7:
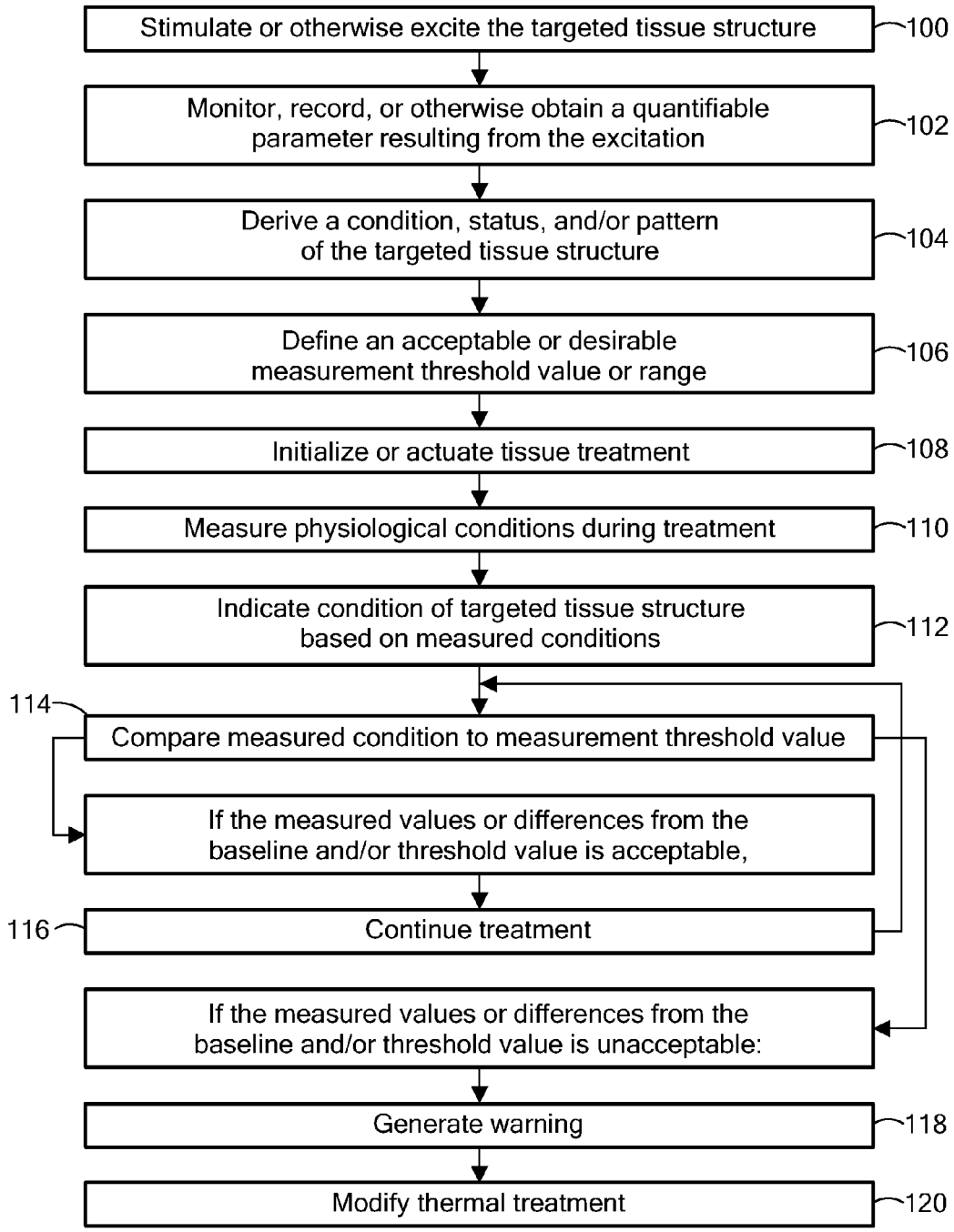
FIG. 7 is a flow chart illustrating an algorithm for a method of operation of a system in accordance with the principles of the present invention.

Now referring to FIG. 7, a method for preventing unintended nerve or tissue injury is shown. In a particular example, a method for monitoring phrenic nerve activity during treatment of tissue is shown. Primarily, the stimulation device 40 is positioned to deliver an excitation or simulating energy to at least a portion of the phrenic nerve, proximal to the targeted ablation site. Such positioning may include, for example, locating one or more electrically and/or magnetically conductive elements in proximity to the phrenic nerve either subdurally or on the exterior skin of the patient. Once positioned, the stimulation device 40 is activated to stimulate or otherwise excite the targeted tissue structure, here being the phrenic nerve, for example (Step 100). The excitation of the targeted structure may be achieved through the delivery of one or more types of excitation energy (such as electrical, magnetic, chemical, or the like) at a predetermined volume, rate, and/or time duration.

Upon excitation, the assessment device 44, placed distally from the targeted ablation site for example, may monitor, record, or otherwise obtain a quantifiable parameter resulting from the excitation (Step 102). For example, the assessment device 44 may obtain EMG readings, MMG recordings, EtCO2 measurements, or the like as discussed above. The measured values may then be processed by filters, amplifiers, or the like to eliminate artifacts, adjusted for attenuation due to fatigue, etc., and conveyed to a processing unit or component, such as those of the console 34. A condition, status, and/or pattern of the phrenic nerve may then be derived or otherwise indicated (Step 104) based at least in part on the stimulation energy delivered in Step 100 and/or the processed measurements obtained in Step 102. For example, a volume or level of excitation energy delivered to the phrenic nerve may be correlated to the resulting response measurements obtained by the assessment device 44 (e.g., an electrical wattage or current delivered to the nerve resulted in a contraction having a certain force, or a respiratory exhalation having a certain concentration of CO2, etc.). An acceptable or desirable measurement threshold value or range may also be determined or otherwise defined (Step 106).

Once a baseline status or physiological condition has been established, treatment of the selected region of tissue may begin with the medical device 10. In particular, the treatment device or system may be actuated (Step 108). In the case of cryotherapy, this may include delivery of a refrigerant or coolant to the catheter. In the case of radiofrequency, microwave, ultrasound, or the like, actuation may include actuation or initiation of the respective energy transducers on the particular device. Physiological conditions then may be measured at selected interims or continuously during treatment by the assessment device 44 (Step 110). A current or real-time condition, status, and or pattern of the target structure (the phrenic nerve, for example) may then be derived, correlated, or otherwise indicated from the processed physiological conditions (Step 112). The current measurements may then be compared to the original baseline or threshold values (Step 114). If the measured values or difference from the baseline and/or threshold value is acceptable, treatment may continue (Step 116). If the measured values or difference from the baseline and/or threshold value is unacceptable, a warning may be generated (Step 118) and the thermal treatment may then be modified (Step 120). For example, the treatment may be automatically terminated, may be reduced in intensity, application, or temperature, or otherwise adjusted until the monitored conditions reach acceptable levels with respect to the defined threshold (or range).

In the case of treating sources of arhythmogenic tissue in the heart, treatment must typically be delivered at a very specific location. Accordingly, it may not be possible to provide effective treatment by moving the medical device 10 to a new location should the measured physiological values (which indicate an effect on the phrenic nerve) falls outside the defined, acceptable threshold value or range. In such instances, the intensity or application of a particular treatment modality may need to be tempered sufficiently to successfully treat the problematic cardiac tissue while continuing to safeguard the surrounding sensitive tissue structures form unwanted damage.

Stimulating a target tissue, such as the phrenic nerve, and subsequently measuring resulting physiological responses provides for a minimally-invasive, non-intrusive method of inferring or otherwise monitoring thermal impact on the phrenic nerve when treating small, sensitive areas of tissue. The monitoring provides an additional safeguard to prevent unintentional damage and/or disruption of cursory physiological structures and functions when treating maladies such as cardiac arrhythmias.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system, comprising:
   a stimulation device having an active element configured to apply an excitation energy to a target tissue structure;
   an assessment device configured to measure a physiological condition resulting from an applied excitation energy;
   a medical device having a thermal treatment element, the medical device, the stimulation device, and the assessment device all being independently positionable with respect to each other; and
   a controller in communication with the assessment device and the medical device, the controller adjusting the operation of the thermal treatment element of the medical device based at least in part on a measured physiological condition measured by the assessment device.

2. The medical device of claim 1, wherein the assessment device includes at least one of an end-tidal carbon dioxide sensor, an impedance pneumograph and a pulse oximeter.

3. The medical device of claim 1, further comprising a console, the console including the controller and a thermal energy source.

4. The medical device of claim 3, wherein the console includes an excitation energy source in communication with the stimulation device.

5. The medical device of claim 1, wherein the thermally conductive region includes a balloon.

6. The medical device of claim 5, wherein the medical device defines a cryogenic coolant flow path therethrough.

7. The medical device of claim 1, wherein the thermally conductive region includes an electrode.

* * * * *